(12) United States Patent
Miyai et al.

(10) Patent No.: US 6,422,056 B1
(45) Date of Patent: Jul. 23, 2002

(54) METHOD FOR CORRECTING THE EFFECT OF A EFFECT OF A COEXISTENT GAS IN A GAS ANALYSIS AND A GAS ANALYZING APPARATUS USING SAME

(75) Inventors: Masaru Miyai; Kenji Takeda; Kaori Inoue; Masaaki Ishihara, all of Miyanohigashi-machi (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 09/498,553

(22) Filed: Feb. 4, 2000

(30) Foreign Application Priority Data

Feb. 5, 1999 (JP) ............................. 11-028950
Jun. 15, 1999 (JP) ............................. 11-168013

(51) Int. Cl.[7] ............................. G01N 21/00
(52) U.S. Cl. ............................. 73/1.06
(58) Field of Search ............................. 73/1.06, 1.07, 73/23.21; 250/252.1, 339.09, 339.13, 341.5; 422/91

(56) References Cited

U.S. PATENT DOCUMENTS 3,727,450 A  *  4/1973  Luckers ...................... 73/1.07
4,560,873 A  * 12/1985  McGowan et al. .... 250/339.09

* cited by examiner

Primary Examiner—Robert Raevis
(74) Attorney, Agent, or Firm—Oppenheimer, Wolff & Donnelly LLP

(57) ABSTRACT

In analyzing the concentration of an objective component contained in a sample gas by a gas analyzer, an output of the gas analyzer is corrected at a fixed point by applying the relationship between the concentration of a coexistent gas and a span sensitivity of the objective component to make it possible to simply correct the effect of the coexistent gas. In addition, by inputting, at the time of the calibration of the gas analyzer, the information on to what extent the base gas composition differs from the average amount of the actual sample along with the concentration amount of the objective component in the calibration gas, the sensitivity adjustment coefficient is determined by taking into account the effect amount which is previously stored in the gas analyzer, by which the effect amount of the span sensitivity by the difference of the base gas compositions in the calibration gas and the sample gas is suppressed, and the effect of the coexistent gas is canceled to the best possible extent.

5 Claims, 8 Drawing Sheets

Fig. 2

| Component | Group 1 | Group 2 | Group 3 | Group 4 | Group 5 | methanol |
|---|---|---|---|---|---|---|
| 1 | CO (L) | 1.0000e +00 | 1.0000e +00 | 1.0000e +00 | 1.0000e +00 | 1.0000e +00 | ......... |
| 2 | CO (H) | 1.0000e +01 | 1.0000e +01 | 1.0000e +01 | 1.0000e +00 | 1.0000e +00 | ......... |
| 3 | CO₂ | 1.0100e +00 | 1.0200e +00 | 1.0300e +00 | 1.0400e +00 | 1.0500e +00 | ......... |
| 4 | CH₄ | 1.0100e +00 | 1.0200e +00 | 1.0300e +00 | 1.0400e +00 | 1.0500e +00 | ......... |
| 5 | THC | 1.0200e +00 | 1.0300e +00 | 1.0400e +00 | 1.0500e +00 | 1.0600e +00 | 1.3000e +01 |
| 6 | NOₓ | 1.0020e +00 | 1.0040e +00 | 1.0060e +00 | 1.0080e +00 | 1.0090e +00 | ......... |
| ⋮ | ......... | ......... | ......... | ......... | ......... | ......... | ......... |

[Select group] [Group 3]

[SPAN Adjust]

CO₂ concentration
□ 2458ppm   ○ 0.735 vol%   △ 2.352 vol%
▽ 6.99 vol%   ◇ 11.58 vol%

CO₂ concentration
Analyzer A
□ 735ppm   ○ 1.67 vol%   △ 16.0 vol%
Analyzer B
▽ 79.9 vol%   ◇ 735ppm

METHOD FOR CORRECTING THE EFFECT OF A EFFECT OF A COEXISTENT GAS IN A GAS ANALYSIS AND A GAS ANALYZING APPARATUS USING SAME

FIELD OF THE INVENTION

The present invention relates to a method for correcting the effect of a coexistent gas in a gas analysis, and a gas analyzing apparatus using the method.

BACKGROUND OF THE INVENTION

In determining a particular gas component (measurement of an objective component or subjective component) having an absorption spectrum in the infrared region by NDIR (Non-Dispersive Infrared Detection) or FTIR (Fourier Transform Infrared Spectroscopy), there may be cases where the measurement amount (span sensitivity) is affected by the coexistent component which has likewise an absorption spectrum in the infrared region but is separated from the objective component or the coexistent component which does not have an absorption spectrum in the infrared region.

This is based on the premise that, notwithstanding the fact that there may be cases to cause differences in spectral intensity depending on the gas composition (coexistent components) with the same gas components and same gas concentrations, according to the conventional infrared absorption method, the interference between the components is attributed to the fact that a complete separation of an overlapping absorption spectra cannot be performed. In practice, it has been observed in the analysis of automobile gases that $H_2O$ and $O_2$, which are the coexistent components to the span directives of CO and $CO_2$ which are the objective components and do not exhibit a constant concentration, are liable to give effects.

However, since $O_2$ does not absorb in the infrared spectrum and since it is difficult to calibrate the concentration of $H_2O$, they are difficult to analyze under the infrared absorption method.

FIG. 6(A) shows the relations between the coexistent $H_2O$ concentration and the error of the $CO_2$ indication value at the time when various concentrations of $CO_2$ are measured. As the $H_2O$ concentration increases, the error of the $CO_2$ indication value is shown largely to be positive. FIG. 6(B) shows the relation between the coexistent $O_2$ concentration and the $CO_2$ indication value at the time when various concentrations of $CO_2$ are measured by using two gas analyzers. As the $O_2$ concentration increases, the error of the $CO_2$ indication value is shown largely to be negative. In other words, it can be seen that, because the sensitivity calibrations of these gas analyzers are carried out by a standard gas produced on the basis of $N_2$ gas, sensitivity change has been produced in the case where the mixed gas containing $H_2O$ and $O_2$ becomes the base gas.

Although a mechanism explaining the phenomena shown in FIGS. 6(A) and (B) is not fully understood, in one factor it can be presumed that a quenching occurs from the mutual interactions of gas molecules.

FIGS. 7A and 7B show a model where quenching may lead to a variation in the amount of infrared absorption.

The model demonstrates a supposition that the amount of variation in infrared absorption depends on the probability of collision between an objective component X and a coexistent component A along with the size of the reciprocal actions at the time of the collision. That is to say, FIG. 7(A) shows a case where both the probability of collision of the coexistent component A with the objective component X and the reciprocal actions at the time of the collision are relatively small. Because the coexistent component A has little effect upon the equilibrium of the base condition or excitation condition of the objective component X, the concentration of the coexistent component A scarcely affects the amount of infrared absorption by the component X. On the other hand, FIG. 7(B) shows the case where both the probability of collision of a coexistent component B with an objective component X and the reciprocal actions at the time of the collision are relatively large. Because the equilibrium of the objective component X is displaced to the base condition side, new light absorption becomes likely to occur. In other words, due to the presence of the coexistent component B, the absorption concentration of the objective component X becomes relatively large, and the objective component X shows a stronger absorption than the case where the base gas is of the coexistent component A and of the same concentration.

With respect to other mechanisms that can cause the above phenomenon, it is possible that a "collision spreading" mechanism broadens the width of the absorption line because the absorption wavelength is affected by the actions of the objective component itself and the coexistent component.

The phenomenon of "collision spreading" is a problematic matter even for the gas analysis of a fuel battery system which is regarded as a promising automobile power source for the next generation. FIG. 8 shows schematically a general fuel battery system 40 having a methanol supply source 41. $CH_3OH$ from the supply source 41 is supplied to a quality reformer 42, where the $CH_3OH$ is reformed under an optional catalyst to generate a reformed gas. The reformed gas contains, besides $H_2$ gas, unreacted $CH_3OH$, high concentrations of $CO_2$ and $H_2O$ as bicomponents, CO, $CH_2$ and the like as impurities. Accordingly, it is so constituted that the reformed gas, after removing the components (such as CO) which poison a fuel battery 44 at an impurity eliminating part 43, is supplied to the fuel battery 44.

Here, the concentration of the generated $H_2$ gas, $CO_2$, $H_2O$, etc. falls into the range of several % to several tens %, while the concentration of CO, $CH_4$, etc. as impurities is significantly less in the order of ppm. However, in order to favorably operate the fuel battery 44 it is desirable to reduce the concentration of impurities such as CO or the like as much as possible, which requires an accurate measurement of the concentrations. In addition, in order to verify or control the efficiency of $H_2$ gas generation, the concentration of $CH_3OH$ or other hydrocarbons (HC) need to be measured.

Therefore, the above fuel battery system 40, has, a sample gas flow route 46 connected to the gas flow route 45 immediately following the reformer 42. The gas flow route 46 is provided with various gas analysis gauges 47 such as a Non-Dispersive Infrared Detection (NDIR) analyzer, magnetic oxygen meter, Flame Ionization Detector (FID), FTIR, etc. The fuel battery system 40 is configured such that the concentration of the impurities, such as CO, $CO_2$, HC, etc. contained in the $H_2$ gas generated in the reformer 42, are monitored at the output of the reformer 42 or immediately after the impurity eliminating part 43. In the case of measuring the concentration immediately after the impurity eliminating part, a sample gas flow route 49 is connected to a gas flow route 48 which is immediate after the impurity eliminating part 43. The sample gas flow route 49 is provided with a gas analyzer 50 similar to the above gas analyzer 47, and the difference of the outputs of the gas analyzers 47, 50 is taken to make it possible to grasp to what extent the above impurities have been removed in the impurity eliminating part 43. Based on the data, the reformer 42 and impurity. eliminating part 43 are controlled to supply high quality $H_2$ gas to the fuel battery 44.

However, when measuring CO by FTIR or NDIR, for example, there is a possibility for sustaining the effect of $H_2$ gas as the coexistent gas due to the mechanism of spectral intensity variation by the coexistent gas as described above. Furthermore, with respect to FID, the $H_2$ gas in the sample gas is apt to affect the sensitivity in the form of a collapse of balance between the fuel gas ($H_2$ gas) and the auxiliary combustion gas (Air) which are supplied to the detector. With respect to the $O_2$ gauge (gas analyzer for determining the oxygen concentration), the $H_2$ gas which is contained in only the sample gas and not in the calibration gas may affect the sensitivity.

FIG. 3 shows an effect of the $H_2$ gas concentration in the sample gas upon the span sensitivity. Curves A, B, C, and D show variations of the span sensitivity in a CO meter, $CO_2$ meter, THC meter (gas analyzer for measuring the whole hydrocarbon concentration), and $O_2$ meter, respectively. For example, the span sensitivity of the CO meter, is monotonously lowered as the $H_2$ gas concentration becomes larger. The span sensitivity for the $CO_2$ or $O_2$ meter monotonously increases as the $H_2$ gas concentration becomes larger. Further, in the THC meter, the span sensitivity initially decreases with an increase in $H_2$ gas concentration. When the $H_2$ gas concentration passes a critical concentration, the span sensitivity increases with an increase in $H_2$ gas concentration.

In order to accurately measure the concentration of the gases under such conditions, it becomes necessary to correct the portions which is affected by the $H_2$ gas. Here, as the concentration of the $H_2$ gas depends on sample gases, a correction is made in recognition of the information from the measured $H_2$ concentration.

Conventionally, the correction is preformed by obtaining real time information on the change of concentration of the $H_2$ gas (continuous correction). However, it is necessary to apply one or more complicated correction curves which cannot be taken as proximate to the linear state as above. Notwithstanding the very complicated correction, precision is not necessarily sufficient, and due to the difference in the response speed between the $H_2$ gas analyzer and the other component analyzer, adequate time is required for the correction. Such differences may become a cause for errors, thus providing problems such as a loss of precision.

SUMMARY OF THE INVENTION

The present invention has been made in reflection of the situation described above. One object is to provide a method for correcting the effect of a coexistent gas during a gas analysis. The effect of a base gas, namely a coexistent gas, can be corrected simply by suppressing the affecting amount of span sensitivity caused by the difference of the base gas compositions between the calibration gas and the sample gas. A further object is to provide a gas analyzing apparatus applying the method.

In order to attain the above objects, the method for correcting the effect of the coexistent gas in the gas analysis of the first embodiment is so set that, in case of analyzing the concentration of the objective component (gas of the measuring subject) contained in the sample gas by the gas analyzer, the output of the gas analyzer is to be corrected by applying the relationship at a fixed point between the concentration of the coexistent gas and the span sensitivity of the objective component.

In order to practice concretely the above method for correcting the effect of the coexistent gas in the gas analysis, a gas analyzing apparatus is equipped with a gas analyzer for analyzing the concentration of the objective components contained in the sample gas and the operation processing part for processing the output from the gas analyzer. In the operation processing part, the output from the gas analyzer is corrected using the relationship at a fixed point between the concentration of the coexistent gas contained in the sample gas and the span sensitivity of the objective component.

Applying the relationship at a fixed position between the concentration of the coexistent gas contained in the sample gas and the span sensitivity of the objective component, the output from the gas analyzer for measuring the objective component is corrected by the same correction. Accordingly, the above output can be quickly corrected by a simple correction formula and without undergoing the effect of a difference in the response speeds between the analyzers.

The concentration of the coexistent gas contained in the sample gas may be selected from a previously known fixed amount or an amount of variation observed by actually providing a gas analyzer for detecting the concentration. Alternatively, when the change by time of the concentration of the coexistent gas is previously known, the related data may be used as such.

With respect to the method of correcting the effect of the coexistent gas in the gas analysis of a second embodiment, information, which comprises differences of the extent the base gas composition between the calibration gas and the typical actual sample along with the concentration amount of the objective component in the calibration gas is inputted into a gas analyzer at the time of the calibration of the gas analyzer. A sensitivity adjustment coefficient is determined in consideration of the effect amount which is previously stored in the gas analyzer.

According to the above method for correcting the effect of the coexistent gas in a gas analysis, it is possible to correct in advance of the span effect by the coexistent component. When the fluctuation of concentration of the coexistent component is relatively small, additional correction is not required to be made in measuring the sample gas or in processing the data, and the software becomes very simple. Furthermore, as the sensitivity adjustment is carried out simultaneously with the calibration, even in the case of measuring the measuring line having different coexistent concentrations, it suffices with re-calibration to be carried out.

In the above embodiments, it is possible to effectively correct the effects of the components which are difficult to fill in the gas cylinder (high concentration $H_2O$ and the like) and the components having variable concentration in the sample gas ($H_2O$ in engine exhaust gas and $H_2$ gas in fuel battery system). In addition, ordinary low priced $N_2$ balanced calibration gas may be used because a calibration gas containing such a coexistent component is not required.

Furthermore, in the first embodiment, coordinate operation is possible even when the concentration varies to a large degree by monitoring the change in concentration of the coexistent gas. In addition, in the second embodiment the errors can be suppressed to the minimum extent by setting to an average condition.

BRIEF DESCRIPTION OF THE DRAWINGS

FIG. 2 is a plan view showing an exemplary screen of a personal computer displaying a correction table to be used in the gas analyzing apparatus of FIG. 1;

DETAILED DESCRIPTION OF THE PREFERRED EMBODIMENTS

Figure 1:
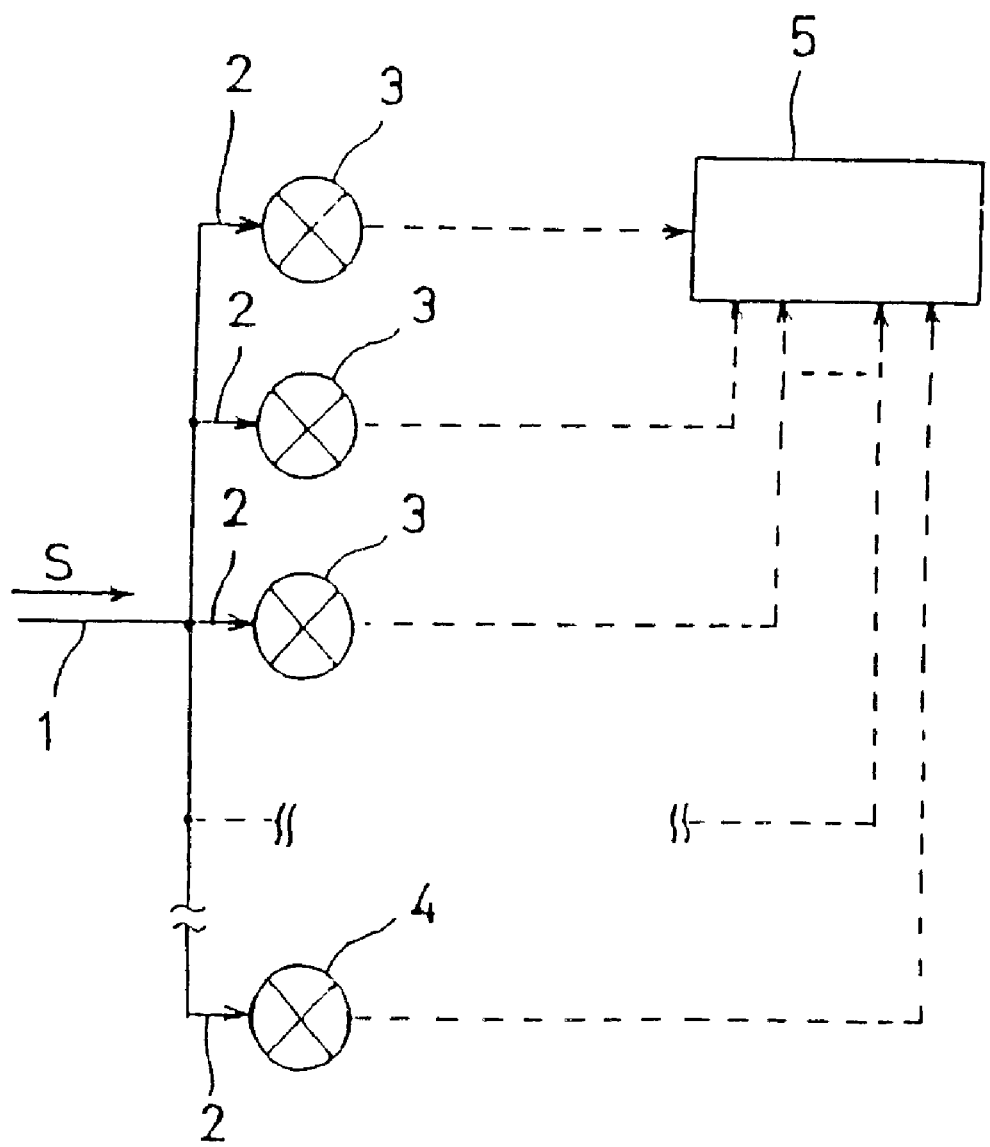
FIG. 1 schematically shows an exemplary gas analyzing apparatus in accordance with a first embodiment of the present invention.

FIG. 1 shows schematically the constitution of a gas analyzing apparatus according to a first embodiment of the invention. The gas analyzing apparatus comprises a gas flow route 1 in which a sample gas S, primarily containing $H_2$ gas, flows. The gas flow route 1 has an upstream portion connected, for example, to a reforming apparatus (not illustrated) for generating $H_2$ gas. A downstream portion of the sample flow route 1 branches into a plurality of flow routes 2 which are mutually parallel with one another. Each branched flow route 2 is provided with a gas analyzer 3 for analyzing the concentration of the gas to be measured such as CO, $CO_2$, THC, etc. contained in the sample gas and an $H_2$ meter 4 for analyzing the concentration of $H_2$ gas, respectively. A personal computer 5 functions as an operation processing unit for obtaining the concentrations of the gas to be measured contained in the sample gas S and $H_2$ gas based on the output signals of a plurality of gas analyzers 3 and $H_2$ meters 4 inputted therein.

In order to eliminate the effects of the $H_2$ gas as a base gas when obtaining the concentrations of the gas to be measured such as CO, $CO_2$, THC, etc. from the respective outputs of the gas analyzer 3 in the personal computer 5, a fixed point correction is made by using the relations between the concentration of the $H_2$ gas contained in the sample gas S and a span sensitivity of an objective component. Hereinafter, an example of the fixed point correction is explained with reference to FIG. 2 and FIG. 3.

Figure 3:
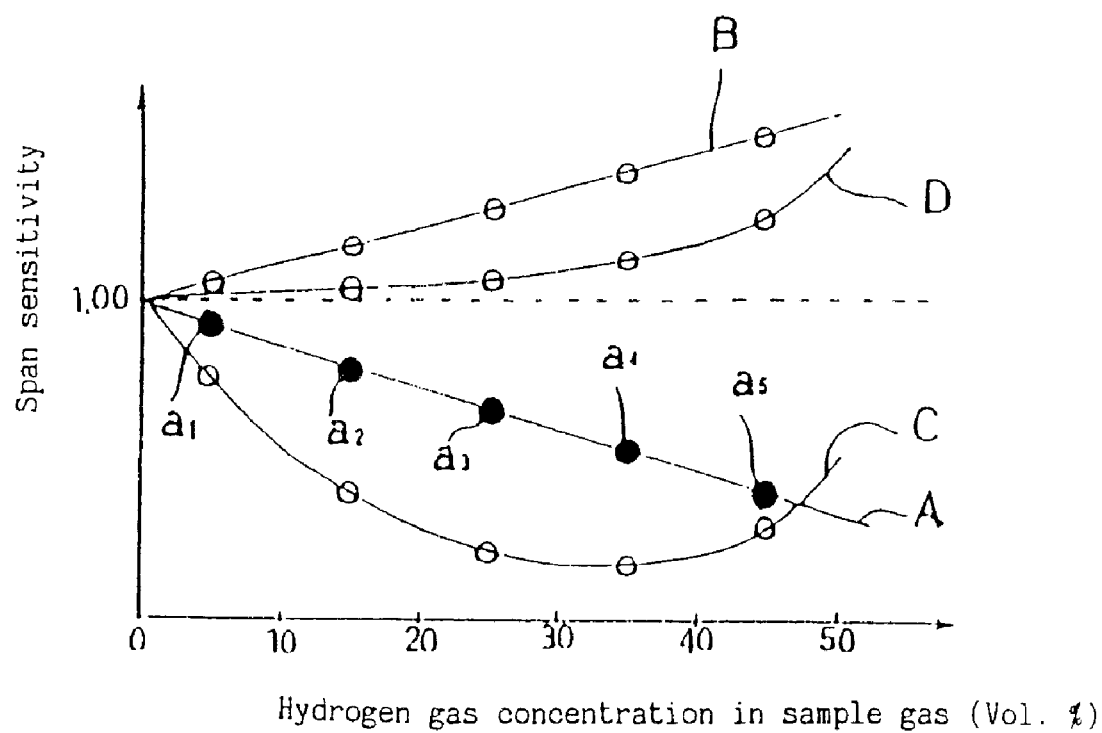
FIG. 3 is a graph showing the relationship between $H_2$ concentration in a sample gas and the span sensitivity of a gas analyzer.

As explained previously, when measuring CO, $CO_2$, THC, etc. with the gas analyzer 3, the span sensitivity is affected when $H_2$ gas is contained in a sample gas S. It is known that there is a relation as shown in FIG. 3 between the $H_2$ gas concentration in the sample gas S and the span sensitivity. That is to say, while the span sensitivity varies in close relation with the variation of $H_2$ gas, it is not desirable to amend this continuously, as already explained. In the first embodiment, as a substitution for this continuous amendment a fixed point amendment is made.

For example, the span sensitivity of the CO meter varies as shown in curve A of FIG. 3, wherein the concentration range of the $H_2$ gas in the sample gas S is classified into groups according to the divisional unit ( e.g. 10 volume %), and correction is made by using the intermediate amount in the group concerned. Parts $a_1$–$a_2$, which are identified with "●", show the amounts to be used when the $H_2$ gas concentrations are 0–10 volume %, 10–20 volume %, 20–30 volume %, 30–40 volume %, and 20–50 volume %, respectively. Similarly, in the $CO_2$ meter, THC meter, and $O_2$ meter, as identified by "O", an intermediate value in each group is to be used.

FIG. 2 shows an exemplary sensitivity correction table using the above values. The correction table is stored in a RAM of the personal computer 5. In the correction table, Groups 1, 2, 3, 4, and 5 correspond to 10 volume % step range of the $H_2$ gas concentrations. For example, in the $CO_2$ meter, if the $H_2$ gas concentration is in a range of 0–10 volume %, 1.01 is used as a correction coefficient. As the set concentration range varies in the step of 10 volume %, the correction coefficient set for the respective range is used. This correction coefficient is automatically selected on the basis of the $H_2$ gas concentration operated in the personal computer 5 based on the output of the $H_2$ meter 4.

The output of each gas analyzer 3 is corrected for example by the following expression (1) in the personal computer 5.

Output after correction=Span correction coefficient× Output of gas analyzer (1)

As described above for the first embodiment, the output from the analyzer 3 for measuring the objective component is corrected at a fixed point by using the relationship between the concentration of the base gas contained in the sample gas S and the span sensitivity of the objective component. Accordingly, it is possible to correct the output of the gas analyzer 3 simply and quickly, and it is also possible to precisely to measure the concentration of the objective component.

In the foregoing embodiment, the concentration of the $H_2$ gas is measured by using the exclusive $H_2$ meter 4 to automatic set the correction coefficient. However, when the time based variation of $H_2$ gas concentration can be determined in advance, the $H_2$ meter 4 may be omitted and the correction coefficient may be manually set via the screen of the personal computer 5. In other words, a group selection is made by using a select group 6 of FIG. 2.

In regards to the first embodiment, an exemplary fuel battery system is given. $H_2$ gas is exemplified as a coexistent gas, but the first embodiment is not limited to it but is extensively applicable to the gas analysis which is susceptible to the effect of the coexistent gas.

As described in the first embodiment, the gas analyzer is so designed that the output from the analyzer for measuring the objective component is corrected at a fixed point by using the relationship between the concentration of the coexistent gas contained in the sample gas and the span sensitivity of the objective component. Accordingly, it is possible to precisely and simply measure the desired gas in the case where the span sensitivity of the gas analyzer changes under effect of the base gas.

Figure 4:
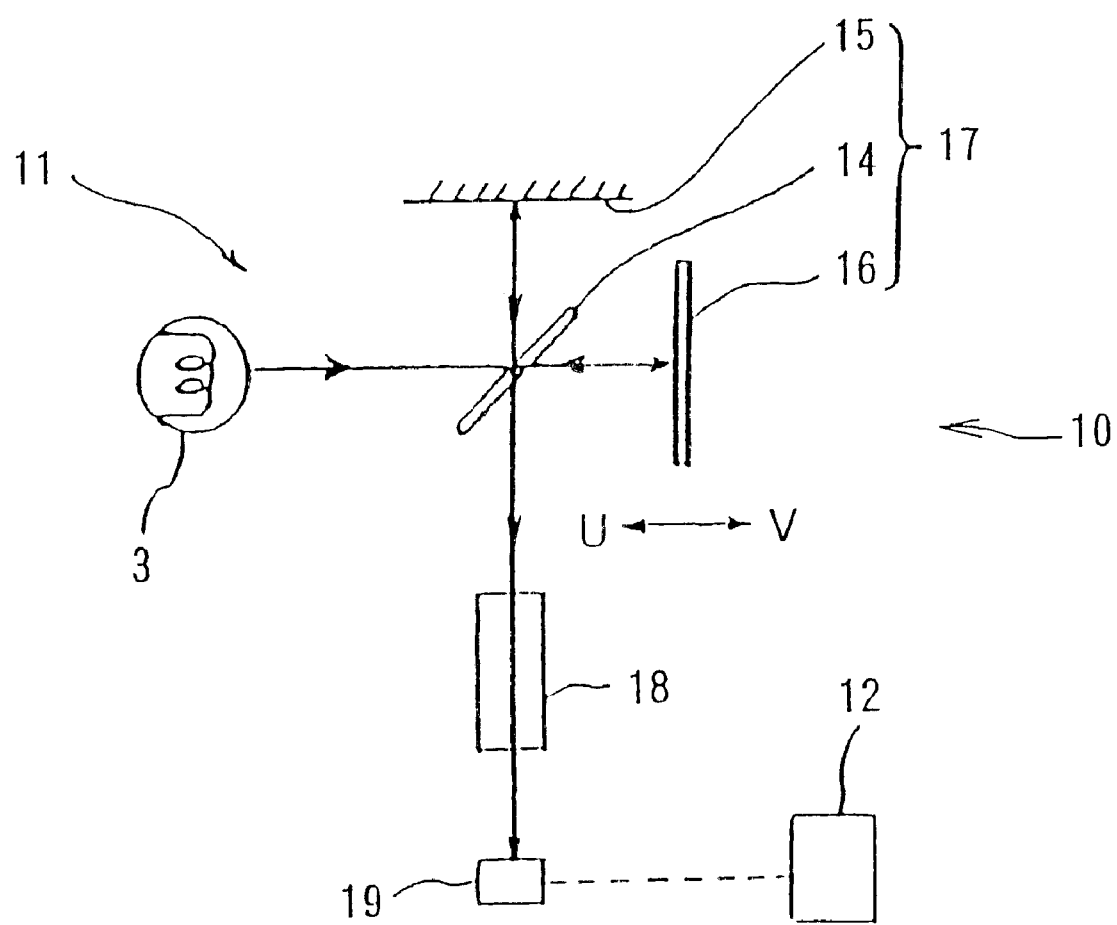
FIG. 4 schematically shows an exemplary gas analyzing apparatus in accordance with a second embodiment of the present invention.

FIG. 4 schematically shows an exemplary gas analyzing apparatus 10 in accordance with a second embodiment of the present invention. The gas analyzing apparatus 10 is constituted as a gas analyzer using Fourier transform infrared spectrometer (hereinafter to be referred to as FTIR gas analyzing apparatus). The gas analyzing apparatus 10 comprises an analyzing part 11, and a data processing part 12 for processing an interferogram which is an output of the analyzing part 11.

The analyzing part 11 comprises an infrared light source 13 which emits parallel infrared rays, an interference mechanism 17 having a beam splitter 14, a fixed mirror 15, and a movable mirror 16 which may move in a direction parallel to line U-V by a non-illustrated driving mechanism, a cell 18 which accommodates the measuring sample, a comparative (reference) sample, etc. and to which infrared light from the infrared light source 13 is irradiated via the interference mechanism 17, and a semiconductor detector 19 or the like.

The data processing part 12 comprises, for example, a computer, and is constituted to arithmetically average the interferogram, carry out Fourier transform of the arithmetic average output at a high speed, and further, based on the Fourier transform output, carry out spectral operation on the component of the subject of measurement.

In regards to the FTIR gas analyzing apparatus 10, a plurality of components can be quantitatively analyzed in the following manner. Namely, a comparative sample or a sample to be measured is accommodated in a cell 18. An infrared ray from the infrared light source 13 is irradiated onto the cell 18 to measure the interferogram of the comparative sample or the sample to be measured. The data processing part 12 subjects the interfergram to Fourier transform to obtain a power spectrum, after which the ratio of the power spectrum of the sample to be compared to the power spectrum of the comparative sample is obtained. The result is converted to a light absorption scale to form an absorption spectrum. Based on the light absorption at the plurality of wave number points in the absorption spectrum, the plurality of components contained in the sample to be measured are quantitatively analyzed.

Hereinafter, the effect of the concentration of the $H_2$ gas in the base gas at the time when CO is measured by using the FTIR gas analyzing apparatus 10 is explained. In Table 1, column ① denotes a relationship between the $H_2$ gas concentration in the base gas and the CO indication (true amount 250 ppm) using FTIR.

TABLE 1

| $H_2$ gas concentration in the sample gas | CO Readings (ppm) | |
|---|---|---|
| | ① on the basis of the $H_2$ gas concentration 0% | ② on the basis of the $H_2$ gas concentration 32% |
| 0% | 250.0 (+0.0 ppm) | 246.4 (−3.6 ppm) |
| 16% | 252.2 (+2.2 ppm) | 248.7 (−1.3 ppm) |
| 32% | 253.6 (+3.6 ppm) | 250.0 (+0.0 ppm) |
| 48% | 254.7 (+4.7 ppm) | 251.1 (+1.1 ppm) |
| 64% | 255.6 (+5.6 ppm) | 251.9 (+1.9 ppm) |
| 80% | 256.1 (+6.1 ppm) | 252.4 (+2.4 ppm) |
| correction coefficient | 1.0 | 0.9858 |

As shown in column ①, the sensitivity is calibrated on the basis of the $H_2$ gas concentration being 0%, and the maximum error due to the coexistence of $H_2$ gas is 6.1 ppm. The ratio of the indication value at 0% $H_2$ gas concentration (250.0 ppm) and the indication value at 32% $H_2$ gas concentration (253.6 ppm) is 0.9858 (250.0/253.6). When the sensitivity is recalibrated at the time of the $H_2$ gas concentration being 32% by using this value, the maximum amount of the error is suppressed to −3.6 ppm, as shown in column ② of Table 1. In the case where the actual $H_2$ gas concentration can be deemed to be in the range of, for example, 16%–48%, the error ranges from −1.3 ppm to +1.1 ppm (according to the calibration based on the $H_2$ gas concentration being 0%, the error ranges from +2.2 ppm to +4.7 ppm). This is within the range of ±0.5% of the true amount (250 ppm), which can be termed as being within a normal practical level.

Figure 5:
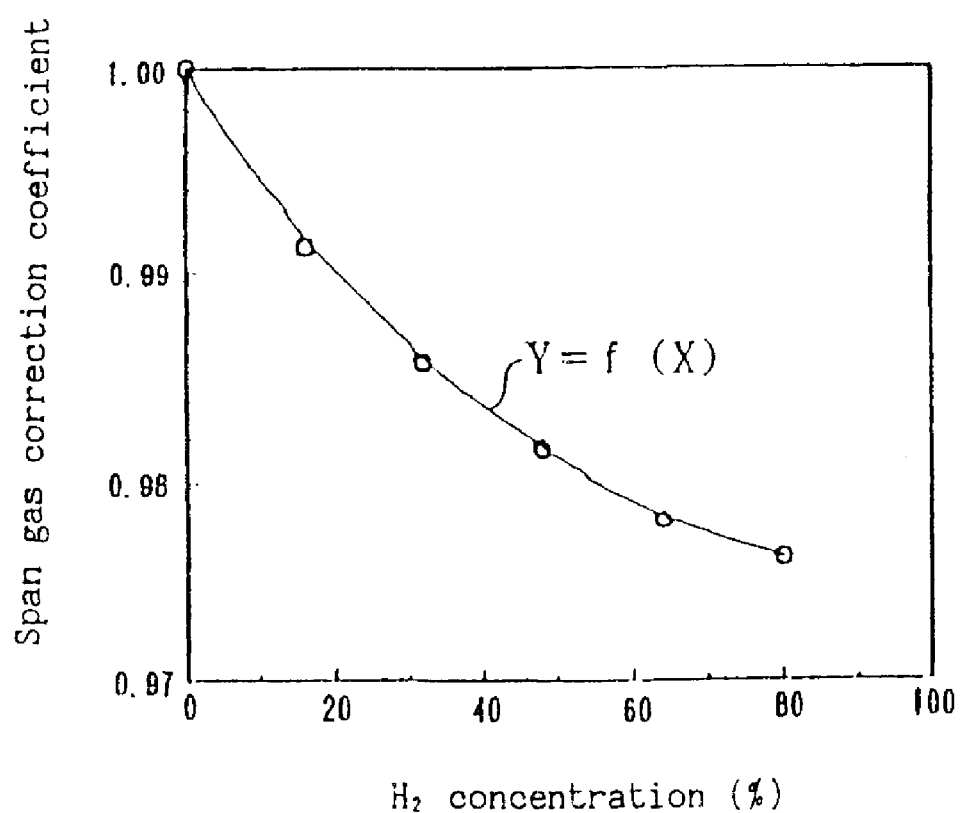
FIG. 5 is a graph showing the relationship between a correction factor and $H_2$ concentration to be used for the second embodiment of the present invention.
Figure 6A:
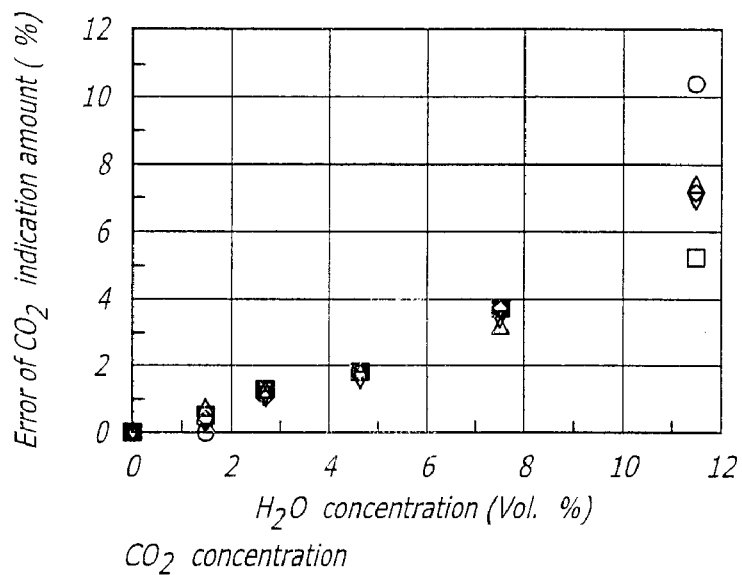
FIG. 6(A) is a graph showing a relationship between the concentration of a coexistent $H_2O$ and the error of a $CO_2$ indication amount.
Figure 6B:
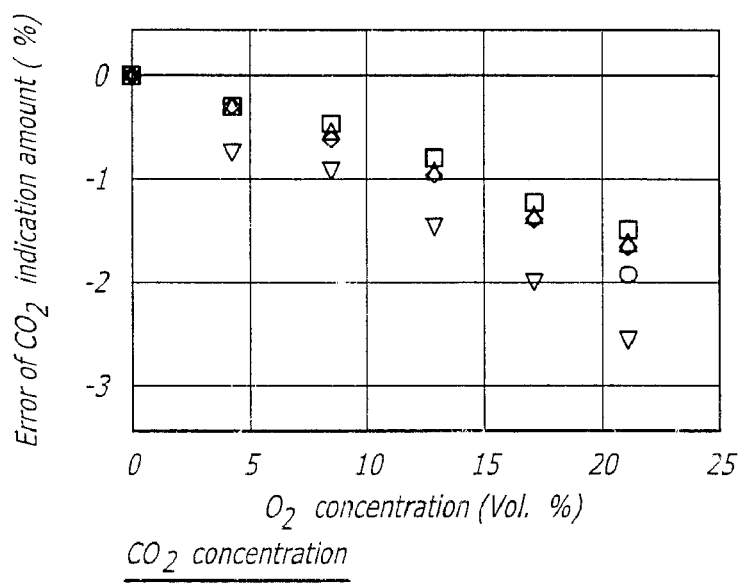
FIG. 6(B) is a view showing a relationship between the concentration of a coexistent $O_2$ and the error of the $CO_2$ indication amount at the time when $CO_2$ of various concentrations are measured by using two analyzers.
Figure 7:
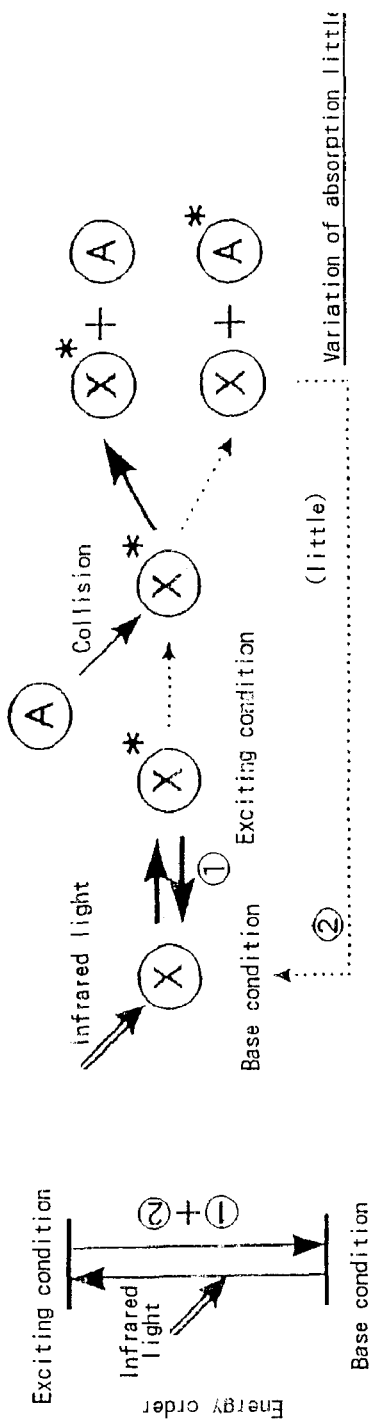
FIGS. 7(A) and 7(B) are models showing a variation in infrared absorption amount due to quenching.
Figure 7:
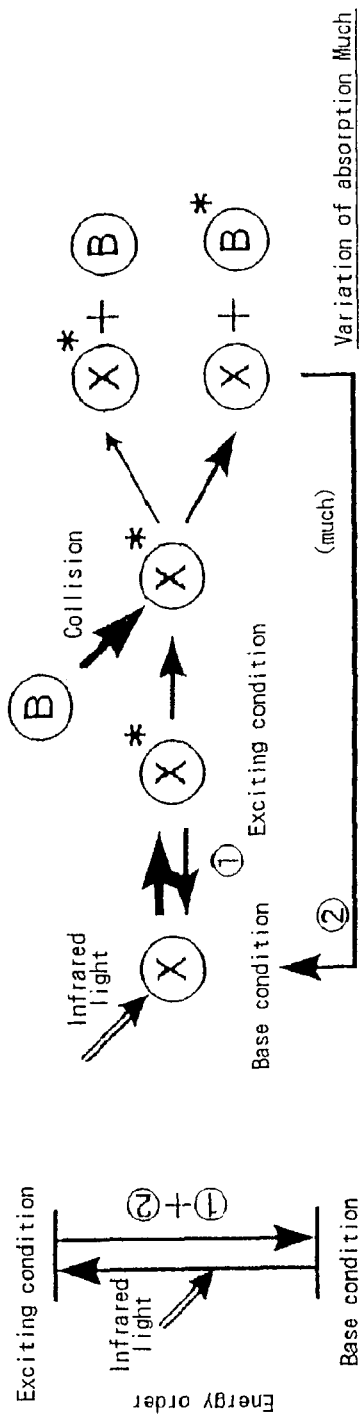
Figure 8:
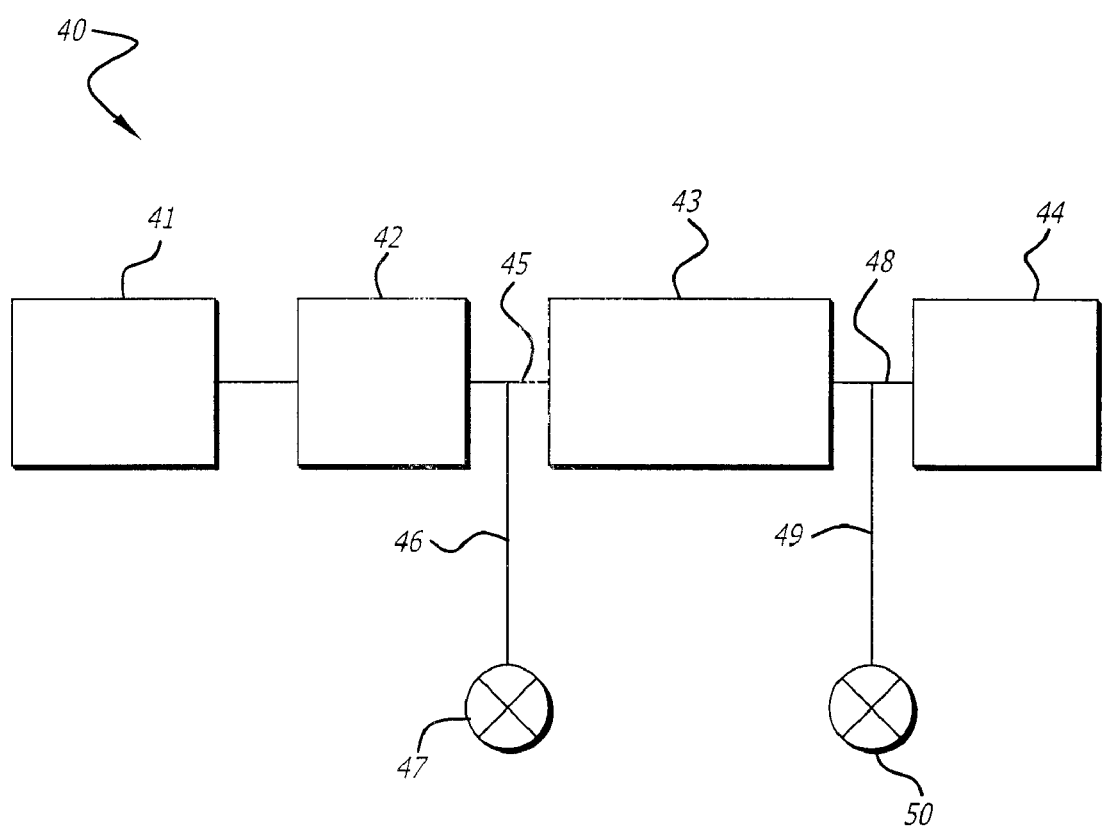
FIG. 8 is a schematic view of a fuel battery system.

Referring to Table 2 and FIG. 5, a correction may be performed from several data points of the $H_2$ gas concentration X in a base gas and from a sensitivity correction coefficient Y (for instance, the numerical value of 0.9858 in the above example). The data points are expressed in the form of an approximate function (order of primary–quarterly expression) Y=f(X), and the function is stored in the operation portion of the analyzer.

TABLE 2

| $H_2$ gas concentration in the sample gas | correction coefficient |
|---|---|
| 0% | 1.0000 |
| 16% | 0.9913 |
| 32% | 0.9858 |
| 48% | 0.9815 |
| 64% | 0.9781 |
| 80% | 0.9762 |

Table 2 represents the ratio between the CO indication value at 0% $H_2$ gas concentration and the CO indication value at each $H_2$ gas concentration. FIG. 5 is a graphic representation of Table 2, wherein the abscissa shows $H_2$ gas concentration and the ordinate shows a span gas correction coefficient.

For example, when the calibration gas has 250 ppm CO ($N_2$ balanced) content and the average or typical $H_2$ gas concentration in the sample gas is 48%, the following results for the cylinder concentration are obtained from the calibration curve:

$$250 \times f(48) = 250 \times 0.9815 = 245.4$$

Thus the amount of 245.4 ppm is employed.

Although the second embodiment refers to a method for correcting the effect of the coexisting gas using FTIR, the second embodiment is not limited to it but may be applied for example to NDIR pursuant to an ordinary infrared absorption method. It is also applicable to the correction of the interference which affects the span point only such as the quenching of chemiluminescence method (CLD).

As described above, the second embodiment is designed to input at the time of the calibration of the analyzer not only the objective component contained in the calibration gas but also the information on the base composition and the sensitivity adjustment coefficient is to be determined in consideration of the effect amount which is previously stored. Accordingly, at the time of the actual measurement no special correction routine is required, and the effect on the span sensitivity by the difference of the base gas composition can be suppressed.

What is claimed is:

1. A method for correcting the effect of a coexistent gas in a gas analysis, comprising:
   providing a gas analyzer apparatus having a plurality of gas analyzers therein to analyze the gas concentration of a sample gas;
   introducing the sample of gas into the gas analyzer apparatus;
   analyzing the sample gas with the plurality of gas analyzers; and
   correcting an output of the plurality of gas analyzers according to a fixed value corresponding to a concentration level of the coexistent gas and a span sensitivity of an objective component.

2. The method of claim 1, wherein the concentration of the coexistent gas is measured with at least one gas analyzer capable of measuring the level of the coexistent gas in the sample gas.

3. A gas analyzing apparatus, comprising:

a plurality of gas analyzers for analyzing the concentration of a measuring subject gas contained in a sample gas; and an operation part in communication with the plurality of gas analyzers for processing an output from the plurality of gas analyzers;

wherein the operation processing part corrects the output from the plurality of gas analyzers according to a fixed value corresponding to a concentration level of a coexistent gas contained in the sample gas and a span sensitivity of an objective component.

4. The gas analyzing apparatus according to claim 3, wherein at least one gas analyzer detects the concentration of the coexistent gas contained in the sample gas, and the output of the at least one gas analyzer is inputted into the operation processing part.

5. A method for correcting the effect of a coexistent gas in a gas analysis, comprising:

providing a gas analyzer apparatus;

pre-storing an effect amount depending on a base gas composition into the gas analyzer apparatus;

inputting information about not only a concentration of an objective component in a calibration gas but about differences in a scan sensitivity of the base gas composition between a scan sensitivity of the calibration gas and a scan sensitivity of a typical sample gas; and determining a scan sensitivity adjustment coefficient by taking into account the effect amount stored in the gas analyzer.

* * * * *

UNITED STATES PATENT AND TRADEMARK OFFICE
CERTIFICATE OF CORRECTION

PATENT NO.     : 6,422,056 B1
DATED          : July 23, 2002
INVENTOR(S)    : Masaru Miyai et al.

It is certified that error appears in the above-identified patent and that said Letters Patent is hereby corrected as shown below:

<u>Title page, Item [54] and Column 1, lines 1-4,</u>
Title, should read -- METHOD FOR CORRECTING THE EFFECT OF A COEXISTENT GAS IN A GAS ANALYSIS AND A GAS ANALYZING APPARATUS USING SAME --.

Signed and Sealed this

Twenty-second Day of July, 2003

JAMES E. ROGAN
*Director of the United States Patent and Trademark Office*